United States Patent [19]

Lourens et al.

[11] 4,133,948
[45] Jan. 9, 1979

[54] MONOSACCHARIDES AND PRODUCTS RESULTING THEREFROM

[75] Inventors: Gerhardus J. Lourens, Randburg; Johannes M. Koekemoer, Pretoria; Elise M. M. Venter, Johannesburg, all of South Africa

[73] Assignee: Chembro Holdings (Proprietary) Limited, Johannesburg, South Africa

[21] Appl. No.: 674,874

[22] Filed: Apr. 8, 1976

Related U.S. Application Data

[63] Continuation-in-part of Ser. No. 565,134, Apr. 4, 1975, abandoned.

[30] Foreign Application Priority Data

Jan. 16, 1975 [ZA] South Africa .................. 75/0317

[51] Int. Cl.$^2$ ..................... C07H 3/02; C07H 9/02
[52] U.S. Cl. ................... 536/1; 260/343.6; 260/347.3; 424/180; 424/279; 536/4; 536/118; 536/119; 536/120
[58] Field of Search .................. 260/343.6; 536/1, 4

[56] References Cited

U.S. PATENT DOCUMENTS 3,297,604  1/1967  Germino ................... 536/1
3,592,808  7/1971  Theander .................. 536/1
3,632,802  1/1972  BeMiller et al. ............ 536/1

OTHER PUBLICATIONS

House "Modern Synthetic Reactions", 2nd Ed., W. A. Benjamin, Inc., Menlo Park, Calif., 1972, pp. 562-563.
Solomons "Organic Chemistry", John Wiley & Sons, Inc., New York, N.Y., 1976, pp. 710-714.

Primary Examiner—Johnnie R. Brown
Attorney, Agent, or Firm—Cushman, Darby & Cushman

[57] ABSTRACT

The invention provides novel compounds of the formula:

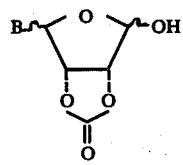

wherein B is $\alpha$- or $\beta$- and represents a hydrocarbyl group in which the $\alpha$-carbon atom is activated by a suitable blocked or unblocked functional group rendering it susceptible to oxidation. The compounds are useful as intermediates in the preparation of prostaglandins and prostaglandin analogues. The invention also provides a stereospecific method of producing these intermediates.

17 Claims, No Drawings

MONOSACCHARIDES AND PRODUCTS RESULTING THEREFROM

CROSS-REFERENCE

This is a continuation-in-part application of our copending application Ser. No. 565,134, filed Apr. 4, 1975, and now abandoned.

This invention relates to novel chemical compounds, processes for their preparation and their use as intermediates. The novel compounds are useful as intermediates in the synthesis of prostaglandins and prostaglandin analogues.

The novel compounds according to the invention are represented by the following general formula:

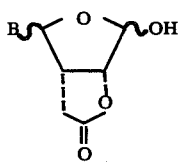

Wherein B is α - or β - and represents a hydrocarbyl group in which the α - carbon atom is activated by a suitable blocked or unblocked functional group rendering it susceptible to oxidation, preferably to an aldehyde.

Preferred compounds of this invention are those in which B represents one of the groups:

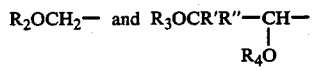

wherein $R_2$, $R_3$ and $R_4$, the same or different, each represents a suitable blocking group and $R_3$ and $R_4$ together may be $>C=O$; and R' and R", the same or different, each represents hydrogen or hydrocarbyl group which is optionally substituted.

Suitable blocking groups are known in the art and are preferably acyl or alkyl blocking groups. Suitable acyl blocking groups have the formula R'''CO- wherein R''' is an alkyl group, which preferably contains 1 to 4 carbon atoms or a phenyl group. The alkyl and phenyl groups may be substituted or unsubstituted. Examples of such blocking groups are acetyl and benzoyl. The alkyl blocking groups are preferably lower alkyl groups containing 1 to 4 carbon atoms which may be substituted. Examples of such blocking groups are trityl, benzyl and methyl.

The blocking groups are preferably acid stable.

The hydrocarbyl groups of R' and R" are preferably lower alkyl of 1 to 4 carbon atoms which may be substituted with groups such as hydroxy or hydroxy blocked by a blocking group as described above. It is preferred that both R' and R" are hydrogen.

Compounds of particular preference of formula I include
5,6-di-O-acyl-3-C-(carboxymethyl-2,3-γ-lactone)-3-deoxy-D-gulofuranose;
5,6-di-O-acyl-3-C-(carboxymethyl-2,3-γ-lactone)-3-deoxy-D-allofuranose;
5-O-acyl-3-C-(carboxymethyl-2,3-γ-lactone)-3-deoxy-D-ribofuranose;
5-O-acyl-3-C-(carboxymethyl-2,3-γ-lactone)-3-deoxy-L-lyxofuranose;
3-C-(carboxymethyl-2,3-γ-lactone)-3-deoxy-D-gulofuranose 5,6-carbonate;
3-C-(carboxymethyl-2,3-γ-lactone)-3-deoxy-D-allofuranose 5,6-carbonate;
3-C-(carboxymethyl-2,3-γ-lactone)-3-deoxy-5-O-methylribofuranose;
3-C-(carboxymethyl-2,3-γ-lactone)-3-deoxy-5-O-methyl-L-lyxofuranose;

The compounds of the general formula I may be converted into compounds of the general formula II, also new compounds:

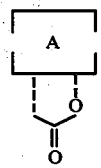

wherein A is selected from:

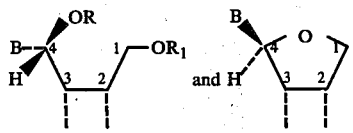

B is as defined for the compounds of formula I and R and $R_1$, the same or different, each represents hydrogen or, together with the oxygen, a leaving group. Leaving groups are those which will leave when reacted with the appropriate nucleophile, e.g. to close the ring. Examples of such leaving groups are sulphonate esters. For example, R and $R_1$ may represent the mesyl, tosyl, benzenesulphonyl or trifluoromethylsulphonyl radicals.

Preferred compounds of Formula II are those in which B is as for the preferred compounds of Formula I, save that $R_2$, $R_3$ and $R_4$ can also be hydrogen.

Compounds of particular preference of formula II are:
5,6-di-O-acyl-3-C-(carboxymethyl-2,3-γ-lactone)-3-deoxy-D-gulitol;
5-O-acyl-3-C-(carboxymethyl-2,3-γ-lactone)-3-deoxy-L-lyxitol;
3-C-(carboxymethyl-2,3-γ-lactone)-3-deoxy-D-gulitol 5,6-carbonate;
3-C-(carboxymethyl-2,3-γ-lactone)-3-deoxy-5-O-methyl-L-lyxitol;
1,4-anhydro-3-C-(carboxymethyl-2,3-γ-lactone)-3-deoxy-D-allitol;
1,4-anhydro-3-C-(carboxymethyl-2,3-γ-lactone)-3-deoxy-D-ribitol;

Compounds of the formulae I and II are useful as intermediates in the preparation of prostaglandins and prostaglandin analogues. For example, compounds of the formula II having the OR and $OR_1$ groups may be ring closed with a suitable nucleohilic reagent so that the stereochemistry at $C_4$ is inverted. The appropriate side chains may be added to the ring closed compounds by oxidation of the B group to an aldehyde followed by coupling of a first side chain and reduction of the lactone ring followed by coupling of a second side chain. These reactions may take place in the reverse order. A most important feature of the particular intermediates of the invention is that the stereochemistry at carbon atoms $C_2$, $C_3$ and $C_4$ is such as to produce prostaglandins and prostaglandin analogues of natural configuration when the side chains are added. It is these prostaglandins which exhibit biological activity.

It is an important feature of the intermediates that the conversion of the compounds of the formula I to the compounds of the formula II is stereospecific at carbon atoms $C_2$, $C_3$ and $C_4$. This means that the stereochemistry at these carbon atoms can be uniquely identified which is of importance in subsequent prostaglandin production.

In particular, the intermediates of the invention are useful in the preparation of a novel class of prostaglandins which show activity as inhibitors of acid production by gastric mucosa and in the constriction or dilation of smooth muscle. These compounds form the subject of a co-pending application of ours, Serial No. 681,742, filed April 29, 1976, and may be represented by the following formula:

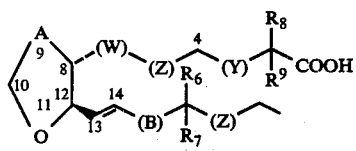  (P)

wherein

A represents —C═O or

B represents

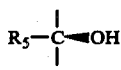

or

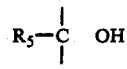

$R_5$ represents H, lower alkyl or substituted lower alkyl

Z represents $CH_2$—$CH_2$ or C═C in the cis configuration $R_6$ and $R_7$, the same or different, represent H or substituted or unsubstituted lower alkyl;

W is —S—, —O— or —$CH_2$—

Y is —S—, —O— or, —$CR_{10}R_{11}$—

$R_8$, $R_9$, $R_{10}$ and $R_{11}$, the same or different, represent H, substituted or unsubstituted lower alkyl or halogen;

the tetrahydrofuran ring may be substituted at the position C 10 with a hydroxy or substituted hydroxy function and when so substituted may form a ring system with a 9-hydroxy substituent; and esters thereof.

Compounds of the general formula I may be prepared by the stereospecific route described diagramatically in the attached scheme. The significance of this route is that the starting materials are sugars of known absolute configuration and each step is stereospecific. Consequently, the absolute stereochemistry of the compounds I is known as well as that of compounds II. This, as mentioned above, is important in prostaglandin production in which the stereochemical relationship of groups is important.

In the attached scheme, B of formula III is as in formulae I and II whereas B in formulae IV → VIII and XI is as in formulae I and II, save that when B is as defined for the preferred compounds $R_3$ and $R_4$ may also form part of an acetal.

Referring to the scheme (a) Compounds of type III such as D-glucose, D-xylose and L-arabinose, whose absolute stereochemical configuration is known, are converted by known methods into compounds of formula

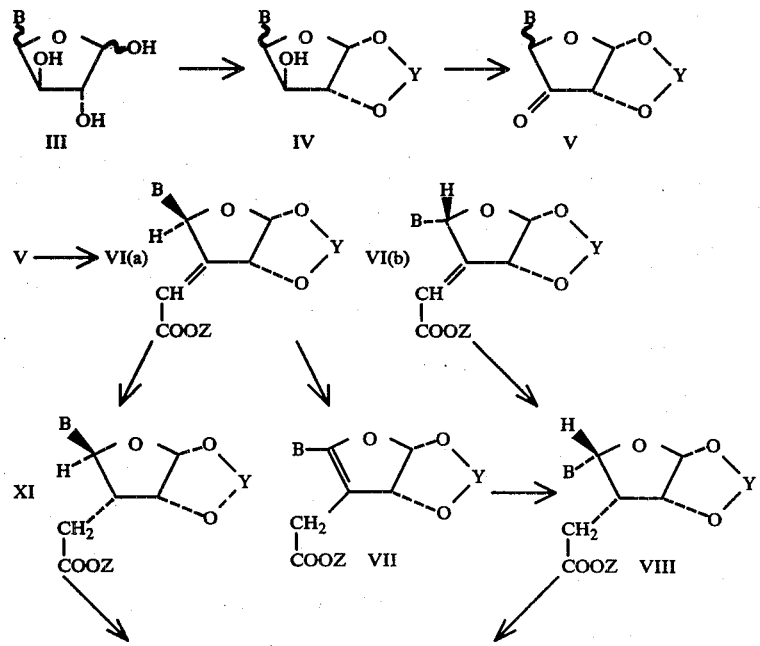

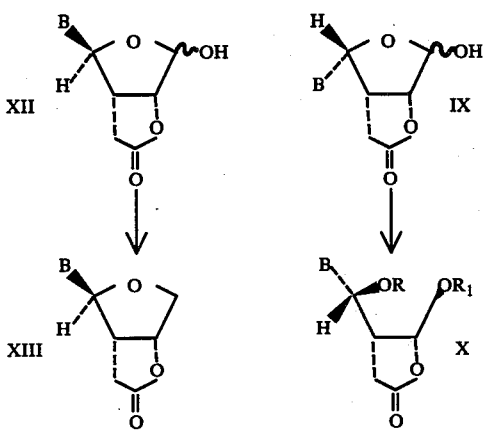

IV wherein Y is a group of the formula

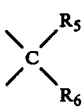

and $R_5$ and $R_6$, the same or different, are alkyl, preferably lower alkyl of 1 to 4 carbon atoms, hydrogen or a carbocyclic group of 4 - 6 carbon atoms. In particular Y may be isopropylidene or cyclohexylidene.

This reaction involves the formation of a cyclic acetal which, as is known in the art, is achieved by contacting a compound of the type III in anhydrous conditions with a ketone or an aldehyde and an acid. Suitable acids are concentrated phosphoric acid, concentrated sulphuric acid, anhydrous zinc chloride, anhydrous $BF_3$, and anhydrous cupric sulphate.

(b) Compounds IV are oxidized to compounds V for example using either ruthenium tetroxide (Lawton, B. T, Szarek, W. A. and Jones, J. K. N. Carbohydrate Research 10, 456-458, 1969) or dimethylsulphoxide and anhydride such as $P_2O_5$ (Onodera, K, Hirano, S and Kashimura N. Carbohydrate Research 6 276-285, 1968) or acetic anhydride (Sowa, W Can. J. Chem., 46, 1586, 1968).

(c) Depending on the configuration, compounds V are converted to compounds VIa or VIb, wherein Z represents a hydrocarbyl group, by for example a Wittig reaction (Rosenthal, A and Nguyen, L Benzing. J. Org. Chem. 34 1029, 1969) or by a Reformatsky reaction followed by water elimination (L. F. Fieser and W. S. Johnson, J. Am. Chem. Soc., 62, 575 (1940)).

Compounds VIa have the B group in the β-position and compounds VIb have the B group in the α-position.

Suitable hydrocarbyl groups are alkyl groups having 1 to 10, preferably 1 to 4, carbon atoms which may be substituted. The substituent may, for example, be a phenyl group. Particular examples of hydrocarbyl groups are methyl, ethyl, propyl and benzyl.

(d) Compounds VIa are isomerized to novel compounds VII by the use of a suitable base. Suitable bases are DBN (1,5-diazabicyclo-{4,3,0}-non-5-ene) or triethylamine or solid bases such as metal alkoides in the presence of an inert solvent.

The base may be used as a suspension in an inert solvent such as benzene.

(e) Compounds VII are reduced stereospecifically from the β-face by methods known to the art, such as by catalytic reduction using, for example, palladium on carbon (Rosenthal A and Nguyen, L. Benzing. J. Org. Chem. 34, 1029, 1969) or Raney-Nickel in an alcohol to give compounds of type VIII.

Such reductions are well known in the art. They involve contacting the compound to be reduced with a catalyst in the presence of hydrogen gas. Generally, the reactions take place in a closed vessel using hydrogen gas of 1 to 5 atmospheres pressure and catalyst in an amount of 1 to 10 percent by weight of the compound to be reduced.

(f) Compounds VIb may be converted directly into compounds VIII by stereospecific reduction from the β-face as described in paragraph (e).

If VIII contains blocking groups $R_2$, $R_3$ and $R_4$ which are acid labile they are selectively removed and replaced by acid stable groups, for example alkylidene to diacyl.

The selective removal of the acid labile groups may take place under the same conditions as described below in paragraph (g).

The formation of the acid stable groups will generally take place using an acyl halide or anhydride in the presence of a nitrogenous base such as pyridine or imidazole. The reaction may, if desired, take place in an inert solvent such as chloroform.

(g) Compounds VIII are converted to novel compounds IX by removal of the blocking group Y using aqueous acid. In the case of organic acids, the acid will in general be present in an amount of 60 to 90 v/v percent. Suitable organic acids are for example acetic, formic, oxalic and propanoic acids. In the case of mineral acids, the amount of mineral acid will be somewhat less and will generally be in the range 5 to 10 v/v percent. The reaction takes place quicker on heating and is usually carried out at a temperature of between 25° C. and 100° C. Particular examples of suitable aqueous acids are acetic acid/water and HCl/aqueous dioxane.

(h) Compounds IX are converted to novel compounds of type X wherein R and $R_1$ = H by reduction, for example with Raney-Nickel in a hot alcohol. Where OR and $OR_1$ represents a leaving group, the alcohol prepared as described may be esterified using known methods with the appropriate reagent, for example mesylchloride in pyridine/solvent. Compounds IX are a group within the group of compounds defined by formula I and compounds X are a group within the group of compounds defined by formula II. In IX and X B, R and $R_1$ have the same meanings as in formulae I and II respectively.

(i) Compounds of formula VIa are converted to XI by stereospecific reduction from the β-face, as described in paragraph (e). Compounds of type VIII may occur as a by product of this reaction sequence.

If XI contains blocking groups $R_2$, $R_3$ and $R_4$ which are acid labile they are selectively removed and replaced by acid stable groups as described above.

(j) Compounds XI are converted to compounds XII by removal of the blocking group Y with aqueous acid to give novel compounds XII in the manner described - paragraph (g). Compounds XII may be converted into compounds XIII by reaction with a suitable haloacid in a solvent such as a dry acid or dry non-hydroxy solvent optionally containing an acid chloride; or by anhydride treatment followed either by reduction of the halo substituted intermediate with a suitable catalyst, such as 10% palladium on carbon in the presence of hydrogen and a nitrogeneous base, such as a trialkylamine; or by reaction with the salt of an alkyl or aryl mercaptan to give the corresponding mercapto-intermediate followed by desulfurization, for example, with Raney-Nickel, or by acylation of the hydroxy function and treatment with an alkyl or aryl mercaptan in the presence of a Lewis acid such as $BF_3$-etherate to give the corresponding mercapto-intermediate followed by desulfurization, for example, with Raney-Nickel. Alternatively, compounds XII may be converted into compounds XIII by treatment with a suitable acid chloride or anhydride followed by reaction with a suitable haloacid in a dry nonhydroxylic solvent. The halo substituted intermediate is then treated in the manner described above to give compounds XIII.

(k) Compounds XII are a group within the group of compounds of formula I and compounds XIII are a group within the group of compounds of formula II. B in compounds XII and XIII has the same meaning as in formulae I and II, respectively.

The invention also includes within its scope a process of the type described above starting at any stage and proceeding to finality and the preparation of the various novel intermediates.

The novel compounds and the processes for their preparation are further illustrated in the Examples that follow in which parts by weight (w) and parts by volume (v) bear the same relationship as the kilogram to the liter.

1. Preparation of
1,2:5,6-di-O-isopropylidene-α-D-glucofuranose (compound of type IV).

Anhydrous D-glucose (600w), dry acetone (4000v), anhydrous pulverized zinc chloride (480w) and 89% O-phosphoric acid (30v) and anhydrous copper sulphate (100w) were mechanically stirred for 30 hours at room temperature. Undissolved glucose was filtered and washed with acetone. The filtrate was cooled to 0°–5° C., made alkaline with sodium hydroxide (340w in 340w water) and filtered. The filtrate was evaporated under reduced pressure to remove solvent, the residue diluted with water and extracted with chloroform. The combined chloroform extract was washed with water, concentrated, dried and evaporated to give crude product (462w, 91% on recovered glucose), white crystals, mp 95°–101° C. Recrystallization from hexane/chloroform (2;1) afforded 1,2: 5,6-di-O-isopropylidene-α-D-glucofuranose, mp 105°–109° C.

2. Preparation of
1,2:5,6-di-O-isopropylidene-α-D-ribohexofuranos-3-ulose (type V) using ruthenium dioxide.

1,2:5,6-di-O-isopropylidene-α-D-glucofuranose (80w) was dissolved in 500v warm carbon tetrachloride. Saturated sodium bicarbonate solution (100v) was added at room temperature to give a two phase mixture. Ruthenium dioxide (1w) was dissolved in 100v 10% sodium metaperiodate and the resulting ruthenium tetroxide extracted into carbon tetrachloride. The extract was added to the well stirred two phase mixture. Whenever the solution turned black, a 10% aqueous sodium metaperiodate solution was added until a yellow-green colour appeared. The reaction was followed by thin layer chromatography on silica gel using hexane/ethyl acetate (3:2). When the reaction was complete, isopropyl alcohol (10v) was added and the mixture filtered through celite. The carbon tetrachloride layer was washed with aqueous sodium thiosulphate and evaporated under reduced pressure to give the hydrate of the ketone. Distillation of the hydrate at 120° C. bath temp, 0.1 mm Hg vacuum gave 1,2:5,6-di-O-isopropylidene-α-D-ribohexofuranos-3-ulose. (78% yield) I.R. ($CHCl_3$) 1 mm light path, $\nu$ max 1770 cm$^{-1}$ (C═O).

3. Preparation of
1,2:5,6-di-O-isopropylidene-α-D-ribohexafuranos-3-ulose (type V) using dimethylsulphoxide and acetic anhydride.

A well shaken mixture of 1,2:5,6-di-O-isopropylidene-α-D-glucofuranose (26w) in dimethylsulphoxide (150v) and acetic anhydride (100v) was left for 48 hours at room temperature. Solvents were removed by distillation in vacuo and the residue distilled at 0.1 mm Hg at a bath temperature of 120° C. to give an oil (21w). I.R. ($CHCl_3$) 1 mm light path $\nu$ max 1770 cm$^{-1}$ (C═O). Sowa, W. Can. J. Chem. 46, 1586, 1968.

4. Preparation of
3-C-Carboethoxymethylene-3-deoxy-1,2:5,6-di-O-isopropylidene-α-D-ribo-hexofuranose (type VIa)

A solution of triethylphosphonoacetate (53,8w), potassium t-butoxide (12w) in anhydrous dimethylformamide (150v) at 0° C. was added to a solution of 1,2: 5,6-di-O-isopropylidene-α-D-ribohexofuranos-3-ulose (42w) in dry dimethylformamide (150v) by positive $N_2$ pressure. The mixture was stirred thoroughly at 0° C. under $N_2$ for one hour and then at room temperature for 48 hours. The solvent was removed in vacuo and hexane added to the residue. After filtration the filtrate was evaporated to dryness under reduced pressure and the semi-crystalline solid purified by chromatography on silica gel using hexane/ethyl acetate initially in the proportion 4:1 (v/v) followed by 3:2 (v/v). A crystalline product (36w) resulted which was recrystallized from petroleum ether bp 40°–60° C. mp 71°–72° C. (needles)

N.M.R. in $CDCl_3$: δ6,34 (q, C-1$^1$H, $J_{1',2}$ = 1,25Hz and $J_{1',4}$ = 2,0 Hz); δ5,84 (d, H-1, $J_{1,2}$ = 4,0 Hz); δ5,72 (two t, H-2, $J_{2,1}$ = 4,0 Hz and $J_{2,1'}$ = 1,25 Hz); δ4,66 (m, H-4); δ4,05 (m, H-5 and H-6); δ4,23 (q, -$\underline{CH_2}$-$CH_3$, J=7,0 Hz); δ1,30 (t -$CH_2$-$\underline{CH_3}$, J=7,0 Hz); δ1,36; δ1,40; δ1,44 and δ1,50 (4s, C($CH_3)_2$).

I R $CCl_4$ 1 mm light path, $\nu$ max 1730 (C═O ester) cm$^{-1}$; 1680 (C═C) cm$^{-1}$.

Analysis Found C 58,47 H 7,31. $C_{16}H_{24}O_7$ requires C 58,52 H 7,36.

5. Preparation of 3-C-Carboethoxymethyl-3-deoxy-1,2:5,6-di-O-isopropylidene-α-D-erythro-hex-3-enofuranose (type VII-novel compounds).

3-C-Carboethoxymethylene-3-deoxy-1,2:5,6-di-O-isopropylidene-α-D-ribo-hexofuranose (10w) was dissolved in dry benzene (5v) and 1,5-diazabicyclo-{4.3.0}-non-5-ene (DBN) (3.73w) was added and the mixture stirred at room temperature (26° C.) under nitrogen for 48 hours. The reaction was followed by thin layer chromatography using silica gel and hexane/ethyl acetate 3:2 (v/v). The disappearance of starting material can be followed by spraying the plate with 9.5% chromic acid in 80% sulphuric acid solution followed by heat. On completion of the reaction the solvent was removed under reduced pressure and the product purified by column chromatography using silica gel and hexane/ethyl acetate 3:2 (v/v) to afford the pure product as a pale yellow oil (7,4w).

N.M.R. in $CDCl_3$: δ5,99 (d, J6Hz, 1H); δ5,31 (d,J6Hz, 1H); δ4,71 (t, J7Hz, 1H); δ4,24–3,91 (m, 4H); δ3,43–3,19 (q, J17Hz, 2H); δ1,43 (s, 9H); δ1,36 (s, 3H); δ1,26 (t, J7Hz, 3H).

I R. $CHCl_3$, 1 mm light path, ν max 1735 (C=O, ester)$cm^{-1}$.

6. Preparation of 3-C-carboethoxymethyl-3-deoxy-1,2:5,6-di-O-isopropylidene-α-D-gluofuranose (type VIII-novel compounds)

Freshly prepared 3-C-carboethoxymethyl-3-deoxy-1,2:5,6-di-O-isopropylidene-α-D-erythro-hex-3-enofuranose (0.1w) in dry ether (5v) was added to palladium black (0.2w) and the mixture shaken under $H_2$ at a pressure of 1,2 kp/$cm^2$ for 5,5 hours. The mixture was filtered and evaporation afforded a crystlline product (0,09w) mp. 80°–82° C. (needles).

N.M.R. in $CDCl_3$: δ5,81 (d, H-1, $J_{1,2}$ = 4,0 Hz); δ4,70 (t, H-2, $J_{2,3}$ = 4,0 Hz).

I R. $CHCl_3$ 1 mm light path, ν max 1735 (C=O ester)$cm^{-1}$.

Analysis Found: C 58,32 H 7,86. $C_{16}H_{26}O_7$ requires C 58,17 H 7,93.

7. Preparation of 3-C-carboethoxymethyl-3-deoxy-1,2-O-isopropylidene-α-D-gulofuranose (type VIII)

3-C-Carboethoxymethyl-3-deoxy-1,2:5,6-di-O-isopropylidene-α-D-gulofuranose (1w) in acetic acid/water 3:2 (v/v) was stirred in an open flask for 30 minutes at 70° C. The mixture was cooled to 0° C. and neutralized with potassium carbonate (3,45w). Acetone (30v) was added and the mixture filtered. The residue was washed with acetone and the combined filtrate was evaporated to dryness. The residue was purified by column chromatography on silica gel using chloroform initially followed by 5% methanol/chloroform (v/v) to afford 3-C-carboethoxymethyl-3-deoxy-1,2-isopropylidene-α-D-gulofuranose (0.2w) as an oil.

N.M.R. in $CDCl_3$ δ5,83 (d, $J_{1,2}$ = 4Hz, H-1); δ4,76 (t, $J_{1,2}$ = 4Hz, H-2); δ3,04 (s, OH); δ4,15 (q, J = 8Hz,-C$\underline{H}_2$ $CH_3$); δ1,26 (t, J = 8Hz,-$CH_2\underline{CH}_3$).

IR. $CHCl_3$. 1 mm light path ν max. 3450 (—OH) $cm^{-1}$; 1720 (—C=O) $cm^{-1}$.

8. Preparation of 5,6-di-O-acetyl-3-C-carboethoxymethyl-3-deoxy-1,2-O-isopropylidene-α-D-gulofuranose (type VIII).

Acetic anhydride (0.74w) and pyridine (0.6w) was added to 3-C-carboethoxymethyl-3-deoxy-1,2-isopropylidene-α-D-gulofuranose (1w) in chloroform (10v). The mixture was stirred for 36 hours at room temperature (26° C.). The mixture was diluted with ice-cold 5% hydrochloric acid and the chloroform solution washed with the acid solution to remove all traces of pyridine. The chloroform solution was washed with saturated aqueous sodium bicarbonate then water, and dried over anhydrous sodium sulphate. Removal of the chloroform under reduced pressure gave 5,6-di-O-acetyl-3-C-carboethoxymethyl-3-deoxy-1,2-O-isopropylidene-α-D-gulofuranose (0,98w).

I R. $CHCl_3$ 1 mm light path ν max 1730 $cm^{-1}$ (C=O, broad).

9. Preparation of 5,6-di-O-acetyl-3-C-(carboxymethyl-2,3-γ-lactone)-3-deoxy-D-gulofuranose (type IX).

5,6-di-O-acetyl-3-C-carboethoxymethyl-3-deoxy-1,2-O-isopropylidene-α-D-gulofuranose (1w) was dissolved in acetic acid/water (20v) 4:1 (v/v) and stirred at 90° C. for 6 hours. The solvent was removed under vacuum and the residual water removed as a benzene azeotrope. The product was purified by column chromatography on silica gel using 2% methanol/chloroform (v/v) to give a crystalline product (0,53w) Mp. 118°–120° C.

IR. $CHCl_3$ 1 mm light path ν max 3450 (—OH) $cm^{-1}$; 1810 (lactone) $cm^{-1}$; 1725 (C=O ester) $cm^{-1}$.

10. Preparation of 5,6-di-O-acetyl-3-C-(carboxymethyl-2,3-γ-lactone)-3-deoxy-1,4-di-O-mesyl-D-gulitol (Type X)

5,6-di-O-acetyl-3-C-(carboxymethyl-2,3-γ-lactone)-3-deoxy-D-gulofuranose (0.3w) was reduced with Raney-nickel (1w) in boiling ethanol (25v) for 1.5 hours. The solution was filtered and the filtrate evaporated to dryness. The residue was dissolved in dry pyridine (5v) and chloroform (5v). Mesyl chloride (0.23w) was added and the mixture left at 0° C. for 16 hours. The chloroform solution was washed with cold 5% hydrochloric acid then aqueous saturated sodium bicarbonate solution and finally water. The solvent fraction was dried over anhydrous sodium sulphate, filtered and evaporated to dryness to give an oil (0,18w).

I R. ($CHCl_3$) 1 mm light path ν max 1790 $cm^{-1}$ (C=O lactone); 1740 $cm^{-1}$ (C=O ester); 1355 $cm^{-1}$ ($SO_2$).

11. Preparation of 3-C-carboethoxymethyl-3-deoxy-1,2:5,6-di-O-isopropylidene-α-D-allofuranose (type XI)

A solution of triethylphosphonoacetate (55w), potassium t-butoxide (15,8w) in anhydrous dimethylformamide (75v) at 0° C. was added to a solution of 1,2:5,6-di-O-isopropylidene-α-D-ribohexofuranos-3-ulose (36.8w) in dry dimethylformamide (75v) by positive $N_2$ pressure. The mixture was stirred thoroughly at 0° C. under nitrogen for one hour and then at room temperature for 48 hours. The solvent was removed in vacuo and the residue extracted with dry hexane (4×100v). The combined hexane extract was filtered and evaporated to give a syrup which crystallized on standing. Raney-Nickel (30w) in methanol (100v) was added and the mixture shaken under $H_2$ (2 atmospheres pressure) at room temperature for 3,5 hours. Filtration and evaporation of the solvent gave a syrup which was purified by column chromatography using silica gel and chloroform as eluent. The product obtained from the column was recrystallized from cyclohexane to give crystalline 3-C-carboethoxymethyl-3-deoxy-1,2:5,6-di-O-isopropylidene-α-D-allofuranose (33,4w) mp 90°–91° C. (needles).

N.M.R. in $CDCl_3$: $\delta 5,75$ (d, H-1, $J_{1,2} = 4,0$ Hz); $\delta 4,78$ (t, H-2, $J_{2,3} = 4,0$ Hz); $\delta 2,32$ (m, H-3); $\delta 4,14$ (q, -$CH_2$-$CH_3$, J=7,0 Hz); $\delta 1,26$ (t, -$CH_2$-$CH_3$, J=7,0 Hz); $\delta 1,29$; $\delta 1,31$; $\delta 1,39$ and; $\delta 1,48$ {4s, $C(CH_3)_2$}.

I R. $CCl_4$ 1 mm light path, $\nu$ max 1730 (C=O ester)$cm^{-1}$

Analysis Found: C 58,33 H 7,88. $C_{16} H_{26} O_7$ requires C 58,17 H 7,93.

In larger scale preparations crystalline 3-C-carboethoxymethyl-3-deoxy-1,2: 5,6-di-O-isopropylidene-α-D-gulofuranose was isolated from the column chromatography described above. The compound was purified by recrystallization from petroleum ether (bp 40°–60° C.), mp 80°–82° C.

12. Preparation of 5,6-di-O-acetyl-3-C-carboethoxymethyl-3-deoxy-1,2-O-isopropylidene-α-D-allofuranose (type XI)

3-C-carboethoxymethyl-3-deoxy-1,2: 5,6-di-O-isopropylidene-α-D-allofuranose (33,4w) in acetic acid/water 4:1 (v/v) (100v) was heated at 70° C. for 40 minutes. The mixture was cooled in an ice bath and potassium carbonate (160w) was added in portions. Acetone (500v) was added and the mixture filtered through a celite pad and the filtrate evaporated. The residue was dissolved in chloroform (250v) and filtered. Evaporation of the filtrate afforded a syrup which was purified by column chromatography using silica gel as stationary phase and first chloroform then chloroform/methanol (97.5:2.5) (v/v) as eluent to give pure 3-C-carboethoxymethyl-3-deoxy-1,2-O-isopropylidene-α-D-allofuranose, (22.4w), colourless oil.

I R. $CHCl_3$ 1 mm light path, $\nu$ max 3500 (OH) $cm^{-1}$; 1735 (C=O ester) $cm^{-1}$.

3-C-carboethoxymethyl-3-deoxy-1,2-O-isopropylidene-α-D-allofuranose (88w) in dry chloroform (50v) was added to dry pyridine (52,7w) in acetic anhydride (68,2w). The mixture was left at room temperature for 28 hours. Chloroform (300v) was added and the mixture extracted first with water, then with 5% hydrochloric acid followed by 5% aqueous sodium bicarbonate. The chloroform layer was dried over anhydrous sodium sulphate filtered and evaporated under reduced pressure to dryness to give a syrup. Purification of the syrup by column chromatography using silica gel and hexane/ethyl acetate (4:1) (v/v) afforded crystalline 5,6-di-O-acetyl-3-C-carboethoxymethyl-3-deoxy-1,2-O-isopropylidene-α-D-allofuranose (88w after recrystallization from petroleum ether bp 40°–60° C., mp 53°–54° C. (needles)

N.M.R. in $CDCl_3$: $\delta 5,79$ (d, H-1, $J_{1,2} = 3,7$ Hz); $\delta 5,08$ (m, H-5); $\delta 4,78$ (t, H-2, $J_{2,3} = 4,0$ Hz); $\delta 4,14$ (q, -$CH_2$-$CH_3$, J=7,0 Hz); $\delta 4,04$-4,50 (m, H-6 and H-6'; $\delta 3,95$ (dd, H-4, $J_{3,4} = 10$ Hz and $J_{4,5} = 5,0$ Hz); $\delta 2,2$-2,9 (m, H-1' and H-3); $\delta 2,02$ and $\delta 2,04$ (2s, $CH_3$-CO-); $\delta 1,48$ and $\delta 1,30$ {2s, $C(CH_3)_2$}; $\delta 1,26$ (t, -$CH_2$-$CH_3$, J=7,0 Hz).

I R. 1 mm light path, $\nu$ max 1740 (broad C=O ester) $cm^{-1}$

Analysis Found: C 54,26 H 6,95. $C_{17} H_{26} O_9$ requires C 54,53 H 7,00.

13. Preparation of 5,6-di-O-acetyl-3-C-(carboxymethyl-2,3-γ-lactone)-3-deoxy-D-allofuranose (type XII)

5,6-di-O-acetyl-3-C-carboethoxymethyl-3-deoxy-1,2-O-isopropylidene-α-D-allofuranose (36,2w) was dissolved in acetic acid/water 4:1 (v/v) (200v) and heated at 90° C. for 3 hours. The solvent was distilled off in vacuo and the residual water removed as a benzene azeotrope. Purification of the residue by column chromatography on silica gel and first hexane/ethyl acetate 3:2 (v/v), followed by 1:1 (v/v) and 2:3 (v/v) as eluents afforded pure 5,6-di-O-acetyl-3-C-(carboxymethyl-2,3-γ-lactone)-3-deoxy-D-allofuranose as an oil (20w).

N.M.R. in $CDCl_3$: $\delta 5,56$ (s, H-1); $\delta 5,18$ (m, H-5); $\delta 4,88$ (d, H-2, $J_{2,3} = 6,0$ Hz); $\delta 4,0$-4,56 (m, H-4, H-6 and H-6'); $\delta 2,40$-3,24 (m, H-1' and H-3); $\delta 2,08$ and 2,10 (2s, $CH_3$-CO-).

I R. $CHCl_3$ 1 mm light path, $\nu$ max 3420 (OH)$cm^{-1}$ 1785 (C=O lactone) $cm^{-1}$ and 1735 (C=O ester) $cm^{-1}$.

Treatment of 5,6-di-O-acetyl-3-C-(carboxymethyl-2,3-γ-lactone)-3-deoxy-D-allofuranose (0,1w) with acetic anhydride (IV) and pyridine (IV) gave after usual isolation crystalline 1, 5, 6-tri-O-acetyl-3-C-(carboxymethyl-2,3-γ-lactone)-3-deoxy-β-D-allofuranose (0,08w), mp. 106°–107° C. (plates)

N.M.R. in $CDCl_3$: $\delta 6,34$ (s, H-1); $\delta 5,09$ (m, H-5); $\delta 4,93$ (d, H-2, $J_{2,3} = 6,0$ Hz); $\delta 4,18$ (dd, H-4, $J_{4,5} = 4,0$ Hz and $J_{3,4} = 8,5$ Hz); $\delta 4,58$-3,88 (m, H-6 and H-6'); $\delta 3,26$-2,40 (m, H-1' and H-3); $\delta 2,04$; $\delta 2,10$ and $\delta 2,11$ (3s, $CH_3$-CO-).

I R. $CHCl_3$: 1 mm light path, $\nu$ max 1785 (C=O lactone) $cm^{-1}$ and 1750 (C=O ester) $cm^{-1}$ Analysis Found: C 50,95 H 5,44. $C_{14} H_{18} O_9$ requires C 50,93 H 5,49.

14. Preparation of 5,6-di-O-acetyl-1,4-anhydro-3-C-(carboxymethyl-2,3-γ-lactone)-3-deoxy-D-allitol(type XIII) via mercapto-intermediates (a) 5,6-di-O-acetyl-3-C-(carboxymethyl-2,3-γ-lactone)-3-deoxy-D-allofuranose (7,2w), 4-nitrobenzoylchloride (5w), pyridine (2,2w) and dry chloroform (100v) were stirred at room temperature for 24 hours. Water (10v) was then added and the mixture stirred for 0,5 hours. The chloroform phase was washed with 1N sulphuric acid, aqueous sodium bicarbonate and water, dried over anhydrous sodium sulphate and filtered. Evaporation of the solvent gave 5,6-di-O-acetyl-3-C-(carboxymethyl-2,3-γ-lactone)-3-deoxy-1-O-p-nitrobenzoyl-D-allofuranose as a syrup (10,4 w). This compound was dissolved in dry dichloromethane (100 v), cooled to 0° C. and dry HBr gas bubbled through for 0,75 hours. The flask was stoppered and kept at 4° C. for 72 hours. The mixture was filtered to remove the p-nitrobenzoic acid formed and the filtrate evaporated in vacuo below 50° C. A solution of thiophenol (2,93 w) and potassium hydroxide (1,35 w) in ethanol (50v) was added to the residue and the mixture warmed on a waterbath (50°–60° C.) for 30 minutes. The solvent was evaporated and the residue purified by column chromatography using silica gel and hexane/ethylacetate 3:2 (v/v) as eluant. The product obtained from the column (7,7 w) gave after recrystallisation from chloroformether crystalline phenyl 5,6-di-O-acetyl- 3-C-(carboxymethyl-2,3-γ-lactone)-1,3-dideoxy-1-thio-α-D-allofuranoside, mp. 113°–115° C. (needles)

N.M.R. in CDCl$_3$: δ7,2-7,56 (m, phenyl); δ5,76 (d, H-1, J$_{1,2}$ = 5,0 L Hz); δ5,20 (dd, H-2, J$_{1,2}$ = 5,0 Hz) and J$_{2,3}$ = 7,5 Hz. Irradiation of the H-1 signal at δ5,76 collapsed the H-2 signal to a doublet of J$_{2,3}$ = 7,5 Hz); δ5,18 (m, H-5); δ4,52-4,0 (m, H-4, H-6 and H-6'); δ3,16-2,44 (m,H-1' and H-3); δ2,04 and 2,08 (2s, $\underline{CH}_3$-CO-).

I R. CHCl$_3$ 1 mm light path, ν max 1790(C═O lactone)cm$^{-1}$ and 1745 (C═O ester) cm$^{-1}$ Analysis Found: C 56,95, H 5,19. C$_{18}$ H$_{20}$ SO$_7$ requires C 56,83 H 5,30.

(b) To a solution of 70 w. 1,5,6-tri-O-acetyl-3-C-(carboxymethyl-2,3-γ-lactone)-3-deoxy-β-D-allofuranose in 300 v dry benzene was added 10,5 v BF$_3$-etherate and 27,5 w thiophenol and the mixture stirred at room temperature for 16 hr. Ether (500 v) was added and the mixture extracted with saturated sodium bicarbonate (2 × 100 v). The organic layer was dried over Na$_2$SO$_4$ and evaporated under reduced pressure. Crystallisation of the residue from chloroform-ether gave 60 w of phenyl 5,6-di-O-acetyl-3-C-(carboxymethyl-2,3-γ-lactone)-1,3-dideoxy-1-thio-α-D-allofuranoside, m.p. 113°–115° C., $\{α\}_D^{23}$ + 248 (c 1,2 CHCl$_3$). The mother liquor (10 w) gave after chromatography on silica gel with first hexane-ethyl acetate (4:1) followed by (3:2) and (1:1) as eluants a further 2 w of the 1-α-phenylmercapto compound and 6 w of the corresponding 1-β isomer (yield: 84% overall).

1-β-phenylmercapto isomer m.p. 82°–3° C. $\{α\}_D^{21,5}$ − 178° (c 3,2 CHCl$_3$)

Analysis: C 56,7 H 5,1 Calc. for C$_{18}$ H$_{20}$ SO$_7$. C 56,8 H 5,3.

N.M.R. (CDCl$_3$ - 60 mHz); δ5,6 (d, H-1 J$_{1,2}$ ≈ 1 Hz); δ5,01 (dd, H-2, J$_{2,1}$ ≈ 1 Hz and J$_{2,3}$ = 6 Hz).

The mercapto-intermediate from (a) or (b) above, (7w) in ethanol (75v) containing Raney-nickel (35w) was refluxed for 2 hours. Filtration and evaporation of the solvent gave 5,6-di-O-acetyl-1,4-anhydro-3-C-(carboxymethyl-2,3-γ-lactone)-3-deoxy-D-allitol (4,5w). Purification by column chromatography on silica gel using first hexane/ethyl acetate 4:1 then 1:1 (v/v) afforded an oil (4w).

N.M.R. in CDCl$_3$: δ5,05 (m, H-2 and H-5); δ4,52-3,92 (m, H-1 and H-6); δ3,85 (dd, H-4, J$_{3,4}$ = 7,5 Hz and J$_{4,5}$ = 5,5 Hz); δ2,95-2,50 (m, H-1' and H-3); δ2,05 and δ2,07 (2s, $\underline{CH}_3$-CO-).

I R. CHCl$_3$ 1 mm light path, ν max 1790 (C═O lactone) cm$^{-1}$ and 1750 (C═O ester) cm$^{-1}$.

Analysis Found: C 52,63 H 5,94. C$_{12}$ H$_{16}$ O$_7$ requires C 52,84 H 5,92.

1,4-Anhydro-3-C-(carboxymethyl-2,3-γ-lactone)-3-deoxy-D-allitol (type XIII novel compounds) A mixture of 5,6-di-O-acetyl-1,4-anhydro-3-C-(carboxymethyl-2,3-γ-lactone)-3-deoxy-D-allitol (4 w) and anhydrous potassium carbonate (4 w) in methanol/water 5:3 (v/v) (40v) was heated for 2 hours at 70° C. The solution was then acidified with Dowex 50 W resin to pH 3, and filtered. The filtrate was evaporated and residual water removed as a benzene azeotrope to give a syrup which crystallized on standing. Recrystallization from methanol/ether or absolute ethanol/ether gave crystalline needles (2,5w), mp. 134°–135° C.

Analysis Found: C 51,04 H 6,31. C$_8$ H$_{12}$ O$_5$ requires C 51,05 H 6,42.

By similar methods the following compounds were prepared:

1. 1,2-O-Isopropylidene-α-D-xylofuranose (type IV compound) from D-xylose (Levene, P.A., Raymond, A.L. J. Biol. Chem. 102, 317, 1933). A colourless oil which slowly crystallized m.p. 34°–40° C.

2. 5-O-Benzoyl-1,2-O-isopropylidene-α-D-xylofuranose (type IV compound). (Levene, P. A., Raymond, A. L. J. Biol Chem 102, 317, 1933. White needles from chloroform/hexane, m.p. 83° C.

I R. CHCl$_3$. 1 mm light path ν max 3470 (-OH) cm$^{-1}$; 1710 (-C═O) cm$^{-1}$; 1600 (-C═C-)cm$^{-1}$.

3. 5-O-benzoyl-1,2-O-isopropylidene-α-D-erythropentofuranos-3-ulose (type V compound) (Tong, G. L., Lee, W. W. and Goodman, L. J. Org. Chem. 32, 1984, 1967) White needles from ether/chloroform/hexane m.p. 94°–95° C.

4. 5-O-benzoyl-3-C-carbomethoxymethyl-3-deoxy-1,2-O-isopropylidene-α-D-ribofuranose (type XI compound-novel compound). Fine white needles from chloroform/hexane m.p. 86°–87° C.

I R. CHCl$_3$ 1 mm light path ν max 1720 (C═O) cm$^{-1}$; 1600 (-C═C-)cm$^{-1}$.

N.M.R. in CDCl$_3$ δ 5,86 ( d,J$_{1,2}$=4H$_z$, H-1 ); δ 4,80 ( t,J$_{2,1}$ = 4H$_z$, H-2 ); δ 3,66 ( s,OCH$_3$); δ 1,50;1,31 (2s, C(CH$_3$)$_2$).

Analysis Found: C 61,66 H 6,21. C$_{18}$ H$_{22}$ O$_7$ requires C 61,70 H 6,33.

5. 5-O-Benzoyl-3-C-(carboxymethyl-2,3-δ-lactone)-3-deoxy-D-ribofuranose (type XII compound-novel compound). Fine white needles from acetone/petroleum ether bp 60°–80° C. mp. 114°–115° C.

I R. chloroform, 1 mm light path δ max 3400 (broad-OH)cm$^{-1}$; 1790 (-C═O lactone)cm$^{-1}$; 1720 (-C═O ester) cm$^{-1}$; 1600 (-C═C-) cm$^{-1}$.

N.M.R. in CDCl$_3$ δ5,60 (s, H-1); δ4,91 (d, J$_{2,3}$ = 6 Hz, H-2).

Analysis Found: C 60,45 H 5,05. C$_{14}$ H$_{14}$ O$_6$ requires C 60,43 H 5,07.

6. 5-O-Benzoyl-3-C-(carboxymethyl-2,3-γ-lactone)-3-deoxy-1-O-(p-nitrobenzoyl)-β-D-ribofuranose Fine white needles from ethyl acetate/petroleum ether bp 60°–80° C. mp 130°–132° C.

I R. CHCl$_3$ 1 mm light path ν max 1800 (C═O lactone)cm$^{-1}$ 1735 (C═O ester)cm$^{-1}$ 1530 (NO$_2$) cm$^{-1}$ N.M.R. in CDCl$_3$ δ6,63 (s, H-1); δ5,19 (d, J$_{2,3}$ = 6 Hz, H-2).

Analysis Found: C 58,68 H 3,98. C$_{21}$ H$_{17}$ NO$_9$ requires C 59,00 H 4,01.

7. Phenyl 5-O-benzoyl-3-C-(carboxymethyl-2,3-γ-lactone) 1,3-dideoxy-1-thio-α-D-ribofuranoside. Fine white needles from ethyl acetate/hexane Mp. 129°–130° C.

I R. CHCl$_3$ 1 mm light path ν max 1795 (C═O lactone)cm$^{-1}$ 1725 (C═O-ester)cm$^{-1}$ N.M.R. in CDCl$_3$ δ5,81 (d, J$_{1,2}$ = 5 Hz, H-1); δ5,23 (dd, J$_{1,2}$ = 5 Hz, J$_{2,3}$ =7,5 Hz, H-2).

Analysis Found: C 64,51 H 4,86. C$_{20}$ H$_{18}$ O$_5$ S requires C 64,85 H 4,89.

8. 1,4-Anhydro-5-O-benzoyl-3-C-(carboxymethyl-2,3-γ-lactone)-3-deoxy-D-ribitol (type XIII compound). Crystalline needles from ethylacetate/petroleum ether bp. 60°–80° C., mp. 130°–133° C.

I R. Chloroform, 1 mm light path; ν max 1785 (C═O lactone) cm$^{-1}$; 1725 (C═O ester) cm$^{-1}$.

N.M.R. in CDCl$_3$ δ8,06-7,22 (m phenyl); δ5,03 (m, H-2); δ4,54-3,90 (m, H-1, H-4, H-5); δ3,00-2,44 (m, H-1', H-3).

Analysis Found: C 64,31 H 5,38. $C_{14}H_{14}O_5$ requires C 64,57 H 5,33.

9. 1,4-Anhydro-3-C-(carboxymethyl-2,3-δ-lactone)-3-deoxy-D-ribitol (type XIII compound). Obtained as an oil which moved as a single spot on silica gel thin layer chromatography (detected with iodine vapour).

I R. $CHCl_3$ 1 mm light path ν max 3490 (broad, OH)$cm^{-1}$ 1790 (C=O lactone)$cm^{-1}$ 10. 5,6-di-O-Benzoyl-3-C-carbomethoxymethyl-3-deoxy-1,2-O-isopropylidene-α-D-allofuranose (type XI compound). Crystals from methanol/ether mp. 63°-65° C. (needles).

I R. in $CHCl_3$ 1 mm light path ν max 1730 (C=O ester)$cm^{-1}$; 1600 (C=C)$cm^{-1}$.

N.M.R. in $CDCl_3$ δ8,08-7,24 (m, phenyl); δ5,83 (d, H-1, $J_{1,2}$ = 4 Hz); δ4,79 (t, H-2, $J_{2,3}$ = 5 Hz); δ3,55 (s, $OCH_3$).

Analysis Found: C 64,14 H 5,71. $C_{26}H_{28}O_9$ requires C 64,48 H 5,82.

11. 5,6-di-O-Benzoyl-3-C-(carboxymethyl-2,3-γ-lactone)-3-deoxy-D-allofuranose (type XII compound). Crystals from ether mp. 123°-124° C.

N.M.R. in $CDCl_3$ δ5,62 (s, H-1); δ4,92 (d, $J_{2,3}$ = 6 Hz, H-2).

I R. $CHCl_3$ 1 mm light path ν max 1780 (C=O lactone)$cm^{-1}$; 1730 (C=O ester)$cm^{-1}$; 1600 (C=C).

Analysis Found: C 64,15 H 4,86. $C_{22}H_{20}O_8$ requires C 64,04 H 4,89.

12. Phenyl 5,6-di-O-Benzoyl-3-C-(carboxymethyl-2,3-δ-lactone)-1,3-dideoxy-1-thio-α-D-allofuranoside. Crystals from chloroform/methanol, mp. 137°-138° C. (needles).

N.M.R. in $CDCl_3$ δ5,82 (d, $J_{1,2}$ = 5 Hz, H-1); δ5,22 (dd, $J_{2,3}$ = 7,5 Hz, $J_{1,2}$ = 5Hz H-2).

I R. $CHCl_3$ 1 mm light path ν max 1790 (C=O lactone)$cm^{-1}$; 1730 (C=O ester)$cm^{-1}$; 1600 (C=C).

Analysis Found: C 66,24 H 4,63. $C_{28}H_{24}SO_7$ requires C 66,68 H 4,79.

13. 1,4-Anhydro-5,6-di-O-benzoyl-3-C-(carboxymethyl-2,3-γ-lactone)-3-deoxy-D-allitol. (Type XIII). Crystals from chloroform/ether, mp. 126°-127° C. (needles).

N.M.R. in $CDCl_3$ δ4,87-4,43 (m, H-1); δ5,11 (m, H-2).

I R. $CHCl_3$ 1 mm light path ν max 1790 (C=O lactone)$cm^{-1}$; 1730 (C=O ester)$cm^{-1}$.

Analysis Found: C 66,68 H 5,00. $C_{22}H_{20}O_7$ requires C 66,65 H 5,09.

14. 5-O-Benzoyl-1,2-O-isopropylidene-β-L-arabinofuranose (Type IV)

Prepared as described (E. M. Acton, K. J. Ryan and L. Goodman J. Am. Chem. Soc., 86, 5352 (1964); E. J. Resist, P. A. Hart, L. Goodman and B. R. Baker ibid, 81, 5176 (1959).

Fine white needles from benzene/petroleum ether bp 40°-60° C., m.p. 146°-147° C.

I R. $CHCl_3$ 1 mm light path ν max 1725 (C=O) $cm^{-1}$ 15. 5-O-Benzoyl-1,2-O-isopropylidene-β-L-threo-pentofuranos-3-ulose (Type V).

Fine white needles from diethylether, mp. 85°-87° C.

I R. $CHCl_3$ 1 mm light path ν max 1727 (C=O ester) $cm^{-1}$ 1780 (C=O ketone) $cm^{-1}$ N.M.R. in $CDCl_3$ δ6,05(d,$J_{1,2}$ = 4Hz, H-1); δ1,50, 1,40(2s, $C(CH_3)_2$).

16. 5-O-Benzoyl-3-C-carboethoxymethyl-3-deoxy-1,2-O-isopropylidene-β-L-lyxofuranose (Type VIII).

A clear syrup which moved as a single spot on silica gel thin layer chromatogrophy (detected with uv light and iodine vapour).

I R. $CHCl_3$ 1 mm light path ν max 1730 (broad, C=O) $cm^{-1}$

N.M.R. in $CDCl_3$ δ5,85 (d,$J_{1,2}$ = 4Hz, H-1); δ4,75 (t,$J_{2,1}$ = 4Hz, H-2); δ4,08 (m,-$CH_2$-$CH_3$, J=7,0 Hz); δ1,60; 1,32 (2s, $C(CH_3)_2$); δ1,20 (t,J=7,0 Hz, -$CH_2CH_3$).

17. 5-O-Benzoyl-3-C-(carboxymethyl-2,3-γ-lactone)-3-deoxy-L-lyxofuranose (Type IX).

Fine white needles from $CHCl_3$/petroleum ether bp 60°-80° C., mp. 111°-112° C.

I R. $CHCl_3$ 1 mm light path ν max 3450 (broad, OH) $cm^{-1}$; 1785 (C=O lactone) $cm^{-1}$; 1725 (C=O ester) $cm^{-1}$.

N.M.R. in $CDCl_3$ δ5,55 (s, H-1); δ4,94 (d, $J_{2,3}$ = 7,0Hz, H-2).

18. 5-O-Benzoyl-3-carboethoxymethyl-3-deoxy-1,2-O-isopropylidene-α-D-glycero-pent-3-enofuranose (Type VII).

Obtained as an oil which moved as a single spot on silica gel thin layer chromatography (detected with iodine vapour).

I.R. $CHCl_3$ 1 mm light path 1750 (broad C=O) $cm^{-1}$; 1610 (C=C) $cm^{-1}$.

The following example illustrates a method of producing a prostaglandin (P) as hereinbefore defined from an intermediate of the formula II.

(a) (3R)-3-{Carboxymethyl-3,4-γ-lactone}-(4R)-4-hydroxy-(2S)-2-{3'-oxo-trans-1'-octenyl}tetrahydrofurane (i)

A mixture of 1,4-anhydro-3-C-(carboxymethyl-2,3-γ-lactone)-3-deoxy-D-allitol (2,5 g) (Formula II) and sodium metaperiodate (2,84 g) in 50 ml. 80% ethanol was stirred at room temperature for 15 minutes.

After the addition of ether (50 ml) the mixture was filtered to remove the precipitated sodium iodate ($NaIO_3$). The filtrate was evaporated in vacuo, the residue taken up in 20 ml ethylacetate, dried over $Na_2SO_4$, filtered and the solvent removed under reduced pressure to give an oil. This was dissolved in 200 ml dry benzene and refluxed in a Dean-Stark apparatus for 45 minutes. Removal of the benzene under reduced pressure gave 1,77 g 1,4-anhydro-3-C-(carboxymethyl-2,3-γ-lactone)-3-deoxy-D-ribitol-5-aldehyde as an oil.

ν max $CHCl_3$ 1780 (C=O lactone) and 1740 (C=O aldehyde) $cm^{-1}$. The compound was not further characterised but immediately used for the next reaction.

To a suspension of sodium hydride (0,272 g 60% dispersion in oil) in 65 ml dry dimethoxyethane (DME) under $N_2$ at 0° C. was added a solution of 1,92 g dimethyl 2-oxoheptyl phosphonate in 10 ml dry DME. The mixture was stirred at room temperature for 30 min, cooled to 0° C., a solution of 1,06 g of the aldehyde produced above in 25 ml dry DME was added and the mixture stirred for a further 2 hr at room temperature. After neutralisation with acetic acid the solution was filtered through celite and the filtrate evaporated to dryness under reduced pressure. The oil obtained was chromatographed on silicagel with ethyl acetate/ n-hexane (1:4 → 2:3) to give 1,39 g of a compound

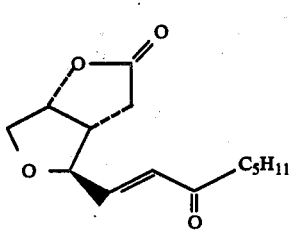
(i)

which crystallised from ether-petroleum ether (40°–60° C.) as plates mp 65°–67° C. $\{\alpha\}_D^{22} + 34°$ (c 0,9 CHCl₃) I R Spectrum ν max CHCl₃ 1790 (C=O lactone) 1680 (C=O) and 1640 (CH=CH) cm⁻¹.

Found : C 66,60; H 7.91. C₁₄H₂₀O₄ requires C 66,67 H 7,99.

N.M.R. in CDCl₃: δ0,87 (3H, t J=7,0 Hz CH₂-CH₃); δ1,2–1,74 (6H, m, -(CH₂)₃-); δ2,54–3,02 (3H, m, H-3 and

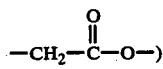

δ3,94–4,23 (2H, m, H-5(α+β)); δ4,32 (1H, t, H-2, J₂,₃ = J₂,₁' = 5 Hz); δ5,08 (1H, m, H-2); δ2,52 (2H, t, J=7 Hz

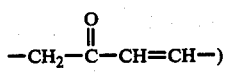

δ6,30 (1H, dd, H-2', J₁',₂' = 15,75 Hz, J₂,₂' = 1,0 Hz); δ6,66 (1H, dd, H-1', J₁',₂' = 15,75 Hz J₂,₁' = 5,0 Hz).

(b)  (3R)-3-{Carboxymethyl-3,4-γ-lactone}-(4R)-4-hydroxy-(2S)-2-{(3'RS)-3'-hydroxy-trans-1'-octenyl}tetrahydrofurane (ii)

To sodium borohydride (1,95 g) in dry dimethoxyethane (50 ml) was added recently fused Zn Cl₂ (3,4 g). The mixture was stirred for 18 hr at 0°–5° C. After filtration under nitrogen, the clear solution (ca 0,5 M) was used immediately.

To 252 mg (i) dissolved in anhydrous DME (4 ml) was added 1,0 ml of the zinc borohydride solution. The mixture was stirred at room temperature until the reduction was complete (about 60 min) saturated potassium hydrogen tartrate was added dropwise until no further evolution of gas was observed. Ethyl acetate (25 ml) was then added, the solution was dried over sodium sulphate, filtered and the filtrate evaporated to dryness to give a colourless oil. This was purified on a silicagel column with chloroform and chloroform/methanol (95:5) to give an oil (245 mg) which crystallised upon standing. Recrystallisation from chloroform-petroleum ether (40°–60°) gave a compound

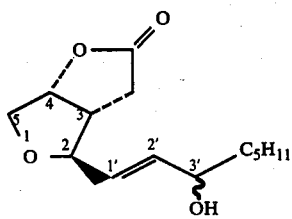
(ii)

as plates, mp 94°–97° C. $\{\alpha\}_D^{22} + 4°$ L C. (C 1,8 CHCl₃) ν max CHCl₃ 3480 (OH) 1780 (C=O), 1610 (CH=CH) cm⁻¹

N.M.R. in CDCl₃: δ0.90 (3H, t, J=6,0 Hz,-CH₂-CH₃); δ1,20–1,60 (8H, m, -(CH₂)₄-); δ2,35–2.98 (3H, m, H-3 and

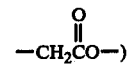

δ3,88–4,27 (4H, m,

H-5(α+β) and H-2; δ5,08 (1H, m, H-4); 5,74 (2H, m, -CH=CH-).

(c)  (3R)-3-{Carboxymethyl-3,4-γ-lactone}-(4R)-4-hydroxy-(2S)-2-{(3'RS)-3'-tetrahydropyranyloxy-trans-1'-octenyl}tetrahydrofurane (iii)

To a solution of 1,02 g (4,017 mmoles) (ii) in anhydrous dichloromethane (10 ml) was added a solution of b 1,5 ml toluenesulphonic acid monohydrate (TsOH) in THF (50 mg TsOH/10ml THF) and 0.66 ml dihydroyrane. The mixture was stirred at room temperature for 30 min. and the reaction was followed by thin layer chromotography (tlc). Pyridine (15 drops) was added and then dichloromethane (40 ml). The solution was washed with a saturated sodium chloride solution, dried over Na₂SO₄ and filtered. Evaporation of the solvent under reduced pressure gave an oil which was purified on a silicagel column with CHCl₃ → 5% MeOH/CHCl₃ to yield 1,31 g of a compound (iii) as an oil with the OH blocked as the tetrahydropyranyl ether. ν max CHCl₃ 1780 (C=O) cm⁻¹ and no -OH absorption.

(d)  (3R)-3-{Formylmethyl-3,4-γ-lactol}-(4R)-4-hydroxy-(2S)-2-{(3'RS)-3'-tetrahydropyranyloxy-trans-1'-octenyl} tetrahydrofurane (iv)

A solution of 1,20 g of (iii) in anhydrous toluene (10 ml) under nitrogen was cooled to −60° C. A solution of 5,8 ml diisobutylaluminiumhydride (20% soln. in hexane) was added dropwise. The mixture was stirred for 20 minutes at −60° C. Excess reagent was destroyed by the dropwise addition of methanol until the evolution of gas ceased. Stirring was continued for an additional 15 minutes at room temperature. Ethyl acetate (50 ml) was added, the solution was dried over sodium sulphate and filtered. Evaporation of the solvent under reduced pressure and purification of the residue on a silicagel column with chloroform → 5% methanol/chloroform gave 1,15 g of oily lactol:

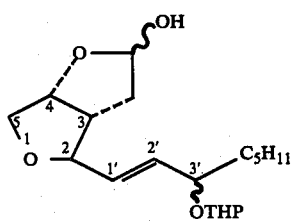
(iv)

ν max CHCl₃ 3420 (-OH) and 1610 (CH=CH) cm⁻¹.

(e) {8R,12S}-(9R,15S)-9,15-Dihydroxy-11-oxa-prosta-cis-5:6-trans-13:14-dienoic acid (va).

A mixture of 0,96 g (24 mmole) of 60% sodium hydride in mineral oil and 10 ml dimethylsulfoxide (DMSO) was stirred under $N_2$ at 70°–75° C. for 45 minutes. The resulting dark solution was cooled to 5° C. To this was added a solution of 5,88 g (12 mmoles) of 4-carboxybutyl-triphenylphosphonium iodide in 10 ml DMSO. The resulting dark-red solution was stirred for 30 minutes at ambient temperature and cooled to 5° C. To this solution was added 1,36 g (4 mmoles) of the lactol produced in the previous step dissolved in 2 ml DMSO. The resulting mixture was allowed to stir for 15 hr. at room temperature. The mixture was added to ice and water (200 ml) and the solution extracted with petroleum ether (40°–60° C.) and ether to remove neutral impurities. The aqueous phase was acidified with oxalic acid to pH2 and extracted with ether (3×50 ml). The organic layer was washed with a saturated sodium chloride solution dried over sodium sulphate and filtered. Evaporation of the solvent in vacuo gave crude product as an oil which was immediately hydrolysed by stirring a solution of it in 10 ml acetic acid/water (7:3) for 4 hr. at ambient temperature. Evaporation of the solvent under reduced pressure below 50° C. yielded an oil (1,82 g). This was chromatographed on preparative tlc plates with glacial acetic acid/ethyl acetate (2:98) to give 500 mg of compound (v) as an oil and 300 mg of the slightly more polar compound (va) as an oil which crystallised upon standing. Compound (va) was recrystallized from ether-petroleum ether (bp 40°–60° C.) at 4° C.

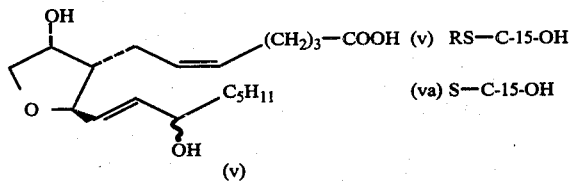

(v) RS—C-15-OH (va) S—C-15-OH

Compound (va) Found C 67,0; H 9,4. $C_{19}H_{32}O_5$ requires C 67,0 H 9,7.

mp 66°–67° C. $\{\alpha\}_D^{26} + 59°$ (c 1,3 -$CHCl_3$)

$\nu$ max $CHCl_3$ 3450 (OH) 1720 (C=O) and 1610 (CH=CH) cm$^{-1}$

N.M.R. in $CDCl_3$ δ0,89 (3H, t, J=6,0 Hz, $CH_2$- $\underline{CH_3}$) δ1,20-2,26 (15H, m, H-8 and $CH_2$ of aliphatic chains) δ2,33 (2 H, t, J=7,0 Hz -$\underline{CH_2}$-$CO_2H$); δ3,77-4,22 (4H, m, H-9, H-10 (α + β) and H-15); δ4,31 (1H, t, H-12, $J_{8,9} = J_{12,3} = 4,0Hz$); δ4,3 (2H, m, H-5 and H-6); δ5,68 (2H, m, H-13 and H-14); δ5,20 (3H, (broad) OH and $CO_2H$ disappears upon addition of $D_2O$).

Enantiomeric mixture (v)

Analysis Found: C 66,9 H 9,5. $C_{19}H_{32}O_5$ requires C 67,0 H 9,7.

$\{\alpha\}_D^{26} + 42$ (c 1,4 $CHCl_3$)

$\nu$ max $CHCl_3$ 3460 (OH), 1720 (C=O) and 1610 (CH=CH) cm$^{-1}$

N.M.R. in $CDCl_3$ δ0,89 (3H, t, J=6,0 Hz, -$CH_2$-$\underline{CH_3}$); δ1,20-2,26 (15H, H-8 and $CH_2$ of aliphatic chains); δ2,34 (2H, t, J=7,0 Hz, - $\underline{CH_2}$-$CO_2H$); δ3,60-4,40 (5H, m, H-9, H-10(α + β), H-12 and H-15); δ5,20 (broad singlet 3H, OH and $CO_2H$ disappears upon addition of $D_2O$); δ5,46 (2H, m, H-5 and H-6); δ5,69 (2H, m, H-13 and H-14).

We claim:

1. A compound of the formula:

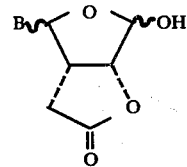

wherein B may be α or β and represents a hydrocarbyl group selected from:

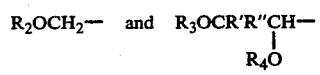

wherein $R_2$, $R_3$ and $R_4$, are the same or different and each represents a blocking group selected from alkyl groups of 1 to 4 carbon atoms which may be substituted with one or more phenyl groups and acyl groups of the formula R'''CO- wherein R''' is an alkyl group of 1 to 4 carbon atoms or a phenyl group, or $R_3$ and $R_4$ together are > C=O and R' and R'', the same or different, each represents a hydrogen or a lower alkyl group of 1 to 4 carbon atoms which may be substituted by a hydroxy group or hydroxy group blocked by a blocking group as defined above.

2. A compound of claim 1 wherein the blocking groups are acid stable and R' and R'', the same or different, each represents a lower alkyl group.

3. A compound of claim 1 wherein the blocking groups are acid stable and R' and R'' are each hydrogen.

4. A compound selected from the group consisting of:
5,6-di-O-acyl-3-C-(carboxymethyl-2,3-γ-lactone)-3-deoxy-D-gulofuranose;
5,6-di-O-acyl-3-C-(carboxymethyl-2,3-γ-lactone)-3-deoxy-D-allofuranose; and
5-O-acyl-3-C-(carboxymethyl-2,3-γ-lactone)-3-deoxy-D-ribofuranose;
5-O-acyl-3-C-(carboxymethyl-2,3-γ-lactone)-3-deoxy-L-lyxofuranose;
3-C-(carboxymethyl-2,3-γ-lactone)-3-deoxy-D-gulofuranose 5,6-carbonate;
3-C-(carboxymethyl-2,3-γ-lactone)-3-deoxy-D-allofuranose 5,6-carbonate;
3-C-(carboxymethyl-2,3-γ-lactone)-3-deoxy-5-O-methyl-ribofuranose;
3-C-(carboxymethyl-2,3-γ-lactone)-3-deoxy-5-O-methyl-L-lyxofuranose.

5. A compound of the formula:

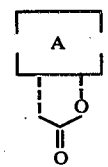

wherein A represents a grouping selected from:

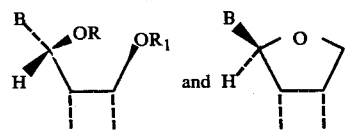

B represents a hydrocarbyl group as defined in claim 1 and R and $R_1$, the same or different, each represents H mesyl, tosyl, benzenesulphonyl or trifluoromethyl sulphonyl.

6. A compound of claim 5 wherein the blocking groups are acid stable and R' and R", the same or different, each represents a lower alkyl group.

7. A compound of claim 5 wherein the acid groups are acid stable and R' and R" are each hydrogen.

8. A compound selected from the group:
5,6-di-O-acyl-3-C-(carboxymethyl-2,3-γ-lactone)-3-deoxy-D-gulitol;
5-O-acyl-3-C-(carboxymethyl-2,3-γ-lactone)-3-deoxy-L-lyxitol;
3-C-(carboxymethyl-2,3-γ-lactone)-3-deoxy-D-gulitol 5,6-carbonate;
3-C-(carboxymethyl-2,3-γ-lactone)-3-deoxy-5-O-methyl-L-lyxitol;
1,4-anhydro-3-C-(carboxymethyl-2,3-γlactone)-3-deoxy-D-allitol; and
1,4-anhydro-3-C-(carboxymethyl-2,3-γ-lactone)-3-deoxy-D-ribitol.

9. A method of preparing a lactone of a compound of claim 1, comprising treating a compound of the formula:

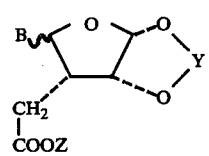

XIV wherein B is as defined in claim 1, and wherein any blocking groups are acid stable, and Y is a group of the formula

$R_5$ and $R_6$, the same or different, are hydrogen or an alkyl or together form part of a carbocyclic ring containing 4 to 6 carbon atoms, and Z is an alkyl group of 1 to 4 carbon atoms which may be substituted with a phenyl group,
with an aqueous acid to remove the Y group and form the lactone of the compound of claim 1.

10. A method according to claim 9 including preparing a compound of formula XIV by:
(a) converting a compound of formula III into a compound of formula IV by reacting compound III with an aldehyde or a ketone in anhydrous conditions in the presence of an acid:

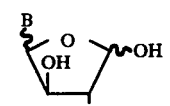

III

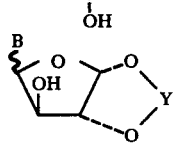

IV wherein B in formula III and formula IV may be α or β and represents a hydrocarbyl group selected from:

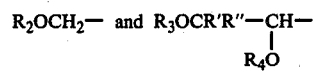

wherein $R_2$, $R_3$ and $R_4$, are the same or different and each represents a blocking group selected from alkyl groups of 1 to 4 carbon atoms which may be substituted with one or more phenyl groups and acyl groups of the formula R'''CO- wherein R''' is an alkyl group of 1 to 4 carbon atoms or a phenyl group, or $R_3$ and $R_4$ together are > C=O and R' and R", the same or different, each represents a hydrogen or a lower alkyl group of 1 to 4 carbon atoms which may be substituted by a hydroxy group or hydroxy group blocked by a blocking group as defined above, and Y is as defined in claim 9

(b) oxidising a compound of formula IV into a compound of formula V, wherein B and Y are as defined for formula IV:

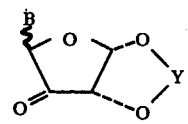

V (c) converting a compound of formula V into a compound of formula VI, wherein B and Y are as defined for formula IV and Z is an alkyl group as defined in claim 13, by condensing a compound of formula V with an α-halo ester to yield a corresponding β-hydroxy ester followed by water elimination to yield a compound of formula VI, or by reacting a compound of formula V with a phosphate ylid to yield a compound of formula VI:

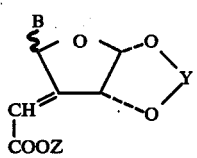

VI (d) stereospecifically reducing the compound of formula VI from the β-face with hydrogen in the presence of a catalyst and selectively removing any acid labile blocking groups replacing them with acid stable blocking groups to yield a compound of formula XIV.

11. A method according to claim 9 including preparing a compound of formula XIV, in which B is in the α-position by:
(a) converting a compound of the formula III' into a compound of the formula IV' by reacting compound III with an aldehyde or a ketone in anhydrous conditions in the presence of an acid:

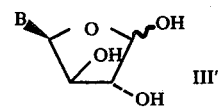 III' 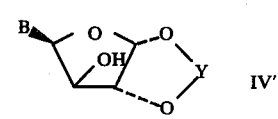 IV' wherein B in the formula III' and formula IV' may be α or β and represents a hydrocarbyl group selected from:

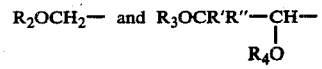

wherein $R_2$, $R_3$ and $R_4$, are the same or different and each represents a blocking group selected from alkyl groups of 1 to 4 carbon atoms which may be substituted with one or more phenyl groups and acyl groups of the formula $R'''$ CO- wherein $R'''$ is an alkyl group of 1 to 4 carbon atoms or a phenyl group, or $R_3$ and $R_4$ together are >C=O and R' and R", the same or different, each represents a hydrogen or a lower alkyl group of 1 to 4 carbon atoms which may be substituted by a hydroxy group or hydroxy group blocked by a blocking group as defined above, and Y is as defined in claim 9;

(b) oxidising a compound of the formula IV' into a compound of the formula V', wherein B and Y are as defined for formula IV':

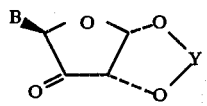 V'

(c) converting a compound of formula V' into a compound of formula VIa by condensing a compound of formula V' with an α-halo ester to yield a corresponding β-hydroxy ester followed by water elimination to yield a compound of formula VIa, or by reacting a compound of formula V' with a phosphonate ylid to yield a compound of formula VIa:

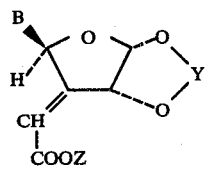 VIa (d) isomerising a compound of formula VIa into a compound of formula VII by the use of a base:

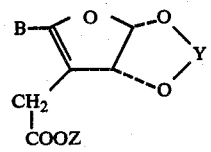 VII

B and Y in formulae VIa and VII being as defined for formula IV' and Z being an alkyl group as defined in claim 13, and (e) reducing a compound of formula VII stereospecifically from the β-face with hydrogen in the presence of a catalyst and selectively removing any acid labile blocking groups and replacing them with acid stable blocking groups to yield a compound of the formula XIV wherein B is in the α-position.

12. A compound of claim 1 wherein the blocking groups are selected from the group of acetyl, benzoly, trityl, benzyl and methyl groups.

13. A compound of claim 5 wherein the blocking groups are selected from alkyl blocking groups of 1 to 4 carbon atoms which may be substituted and acyl blocking groups of the formula $R'''$ CO- wherein $R'''$ is an alkyl group of 1 to 4 carbon atoms or a phenyl group.

14. A compound of claim 5 wherein the blocking groups are alkyl blocking groups of 1 to 4 carbon atoms which may be substituted with one or more phenyl groups.

15. A compound of claim 5 wherein the blocking groups are selected from the group of acetyl, benzoyl, trityl, benzyl and methyl groups.

16. A compound of the formula:

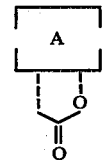

wherein A represents a grouping selected from:

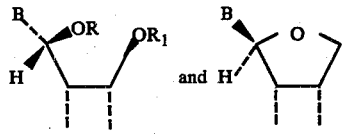

and B may be α or β and represents a hydrocarbyl group selected from:

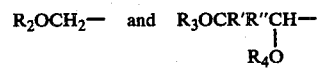

wherein $R_2$, $R_3$ and $R_4$ are the same or different and each represents hydrogen or a blocking group selected from alkyl blocking groups of 1 to 4 carbon atoms which may be substituted with one or more phenyl groups and acyl blocking groups of the formula $R'''$ CO- where $R'''$ is an alkyl group of 1 to 4 carbon atoms or a phenyl group, or $R_3$ and $R_4$ together with >C=O and R' and R" are the same or different and each represents a hydrogen or a lower alkyl group of 1 to 4 carbon atoms which may be substituted by a hydroxy group or a hydroxy group blocked by a blocking group as defined above and R and $R_1$ are the same or different and each represents hydrogen, mesyl, tosyl, benzenesulphonyl or trifluoromethyl sulphonyl.

17. A compound of claim 16 wherein $R_2$, $R_3$ and $R_4$ each represents hydrogen.

* * * * *

UNITED STATES PATENT AND TRADEMARK OFFICE
CERTIFICATE OF CORRECTION

PATENT NO. : 4,133,948
DATED : January 9, 1979
INVENTOR(S) : Gerhardus J. LOURENS; Johannes M. KOEKEMOER; Elise M.M. VENTER It is certified that error appears in the above—identified patent and that said Letters Patent are hereby corrected as shown below:

In the heading of the patent, add in Item [30] omitted priority data as follows:

--Apr. 19, 1975  [ZA]   South Africa....75/1985

Apr. 30, 1975  [ZA]   South Africa....75/2806--

Signed and Sealed this

Eighth Day of July 1980

[SEAL]

Attest:

SIDNEY A. DIAMOND

Attesting Officer       Commissioner of Patents and Trademarks